United States Patent [19]
Vild et al.

[11] 4,024,470
[45] May 17, 1977

[54] EDDY CURRENT DETECTOR FOR HOT TEST PIECES HAVING COOLANT FLUID AND PURGE FEATURES

[75] Inventors: Joseph P. Vild, Lyndhurst; William I. Cleary, Youngstown; Donald P. Fox, Cleveland, all of Ohio

[73] Assignee: Republic Steel Corporation, Cleveland, Ohio

[22] Filed: May 20, 1974

[21] Appl. No.: 471,183

[52] U.S. Cl. .............................................. 324/37
[51] Int. Cl.² ....................................... G01R 33/12
[58] Field of Search ............. 324/37, 40; 73/67.8 S, 73/71.5 U

[56] References Cited
UNITED STATES PATENTS

| | | | |
|---|---|---|---|
| 2,855,565 | 10/1958 | Enders | 324/40 |
| 3,303,691 | 2/1967 | Beaujard et al. | 73/71.5 U |
| 3,694,735 | 9/1972 | Mester | 324/40 |

FOREIGN PATENTS OR APPLICATIONS

| 153,787 | 7/1963 | U.S.S.R. | 324/40 |
|---|---|---|---|

OTHER PUBLICATIONS

Godshall et al., Eddy Current Inspection of Pipe at 250° F. ASME Publication, Sept. 1966, pp. 1–9.
Arnelo et al., Eddy Current Inspection of Hot Rod; Mat. Eval; Nov. 1968, pp. 230–235.
Stumm, W., New Developments in Eddy Current Testing of Hot Wire Rod and Tubes; Non–Destructive Testing, Apr. 1971, pp. 101–105.

*Primary Examiner*—Robert J. Corcoran
*Attorney, Agent, or Firm*—Watts, Hoffmann, Fisher & Heinke, Co.

[57] ABSTRACT

An eddy current flaw detection apparatus which is particularly adapted for inspecting articles at elevated temperatures. A plurality of detectors are supported about at least a portion of a workpiece path of travel to detect and locate flaws in workpieces. A non-magnetic, metallic shield is between the detectors and the workpiece path. A cooling medium is applied to the heat shield to protect the detectors from the heat of a hot workpiece. The cooling medium is also used to purge foreign matter from the assembly.

In one embodiment an exciter and detector assembly is disclosed which is constructed as an integral unit encapsulated within moisture-impervious material. In this embodiment, the assembly is movable relative to the workpiece path.

In another embodiment, the detectors and the exciter surround the workpiece path.

Metallic powder is sprayed on a hot workpiece to mark the location of detected flaws. The heat of the article fuses the marking metal powder in place on the hot workpiece.

7 Claims, 10 Drawing Figures

EDDY CURRENT DETECTOR FOR HOT TEST PIECES HAVING COOLANT FLUID AND PURGE FEATURES

CROSS REFERENCE TO RELATED PATENT AND APPLICATIONS

1. U.S. Pat. No. 3,234,457 issued Feb. 9, 1966 to G. W. Sower et al., entitled "Non-Destructive Eddy Current Testing Device and Method Utilizing Sensing Means Movable Relative to the Excitation Means and Test Piece."

2. U.S. Pat. application Ser. No. 82,051, filed Oct. 19, 1970 by R. G. Baker et al. entitled "Multiprobe Flaw Detection Device and Method of Operation", now abandoned in favor of continuation application Ser. No. 554,167, filed Feb. 28, 1975, (here THE DETECTOR CASE).

3. U.S. Pat. application Ser. No. 471,311 filed May 20, 1974 by J. P. Vild et al. entitled "Flaw Detection Apparatus and Method", now U.S. Pat. No. 3,916,301, here the CIRCUIT CASE).

BACKGROUND OF THE INVENTION

1. Field of the Invention

This invention relates to nondestructive testing of workpieces for flaws and more particularly to the testing for flaws in an elongated article while it is still hot from its fabrication.

2. Description of the Prior Art

In the manufacture of steel and other metal products it is desirable to inspect for flaws and imperfections. With current manufacture most inspect for flaws and imperfections. With current manufacture most inspection is done by or with the assistance of some type of detecting apparatus. Several popular testing apparatrisis for detecting flaws utilize eddy currents.

In one type of eddy current apparatus, a high frequency power source induces eddy current flow in a workpiece being inspected. A detection assembly is positioned in proximity to the workpiece and they are relatively moved along a path of travel to locate any flaws that may be present in the workpiece.

Each detection assembly has one or more detecting coils which are inductively coupled with the workpiece and which effect the flaw detection. This detection results from the capability of a detection coil to produce output signals in response to variations in eddy current flow in the workpiece. These variations are caused by flaws in the workpiece. Accordingly, variations in output signals from the detection coils are indicative of flaws in the article being inspected.

These prior systems have been relatively successful in many applications but none have provided reliable inspection of hot, relatively large, pipe or bar stock immediately after manufacture. There have been proposals for testing immediately after fabrication but such proposed detection apparatus could not withstand fabrication temperatures in many applications.

Because of limitations in the hot inspection capabilities of prior inspection systems, all but very small steel pipe has, of necessity, been permitted to cool for approximately one hour before any flaw inspection was commenced. With present pipe-fabricating machinery, welded pipe can be produced at speeds of the order of 1600 feet of pipe per minute. If a pipe welder is malfunctioning, literally miles of defective pipe may be fabricated before flaw inspection reveals the existence of the malfunction in the welder.

Various proposals have been made for hot inspection of steel pipe, but known proposals have all had drawbacks. For example, proposals have been made to use heat-resistance materials, such as ceramics to protect detectors from heat, but these have not proved particularly practical and successful.

A principal shortcoming of prior proposals is they have not provided adequate heat transfer to maintain the detector transducers cool enough to assure reliable detection and adequate life spans. As a consequence, it has been difficult to obtain good signal-to-noise ratios which are important in obtaining high sensitivity in testing.

Others have proposed magnetic shield assemblies made primarily from metallic materials. Where metal materials have been proposed in such assemblies for positioning between a workpiece and a detector, longitudinal slotting has been considered essential. These slots are to be closed by electrically insulating materials. Such insulated slots were to prevent a loop-like flow of eddy currents which would mask workpiece eddy current flow and cause excessive losses in detection sensitivity. This slotting has been considered necessary because it has been believed that a circular conductive shield would destroy the operability of an inspection device.

If one attempts to apply one of these known slotted shields as a heat shield, one is confronted with a major problem in achieving effective cooling. Thermal expansion will inevitably result in coolant leakage between the metal and the electric insulator.

In a typical prior bar and tube inspector, both an exciter coil and a saturation coil surround the workpiece path of travel. The saturation coil magnetically saturates a workpiece to improve the sensitivity of the testing device. When a steel pipe is tested at a temperature above its Curie point, that is, about 1415° F. for carbon steel, the saturation coils can be eliminated because the pipe is no longer magnetic.

While it has been recognized that the saturation coils may be eliminated, it has been considered necessary to provide fixed exciter coils which usually surround the workpiece path. Accordingly, in devices such as that shown in the DETECTOR CASE, or the earlier Sower et al. U.S. Pat. No. 3,234,457, the amount of radial movement of a detector coil was limited by the surrounding exciter coil and its supporting structure.

There have been proposals to use exciter coils which do not surround a workpiece in inspection apparatus for inspecting only part of a pipe such as a weld. While there have been such proposals, exciter coils have been mounted in fixed positions relative to the paths of workpieces being inspected.

When a flaw inspection device surrounds a workpiece path, most repair and certainly any replacement can only be achieved when there is no workpiece along the workpiece path of travel. If the inspecting device is positioned to inspect pipe continuously rather than in sections, obviously the manufacturing operation must be interrupted to permit the desired repair or replacement.

Another disadvantage of prior inspection devices is they are relatively susceptible to a calamity that can result from what is known as a "cobble". From time to time, pipe coming from a continuous welder pipe forming machine may deviate rather appreciably from its designed and intended path of travel. It can deviate from a path of travel to the extent that it may strike a detecting assembly, even tearing it loose from its mounting. This is a cobble.

Characterization of the consequence of a cobble as a calamity does not seem an overstatement when one considers the possible and in fact probable consequences. The pipe can propel the dismounted detector along with it at speeds of the order of 30 miles per hour. Both the cables connecting the detector assembly to its associated electrical components and the components may be broken or damaged. In short, the entire flaw inspection apparatus can be destroyed by a cobble.

With the construction taught in the DETECTOR CASE and in those situations where only the weld is inspected with the construction taught in the Sower et al. U.S. Pat. No. 3,234,457, the detector coils are protected to some extent from a cobble. They are protected because they are mounted in each case on biased arms which permit detector coil movement radially of the workpiece path of travel. The movement of the detector coils has been limited by the exciter coils which have surrounded both the workpiece and the detection coils. The exciter coils, as has been indicated, are fixed relative to the path of travel.

In small-size pipes where some hot inspection success has been achieved, there is another difficulty. This difficulty is in marking the hot metal at the location of a detected flaw. Conventional marking techniques are not readily adaptable, if adaptable at all, to use on hot products.

SUMMARY OF THE INVENTION

This invention provides eddy current flaw inspection apparatus which overcomes the problems of prior proposals including those problems which have been described. This apparatus is especially suited for the inspection of steel pipe while it is still hot from fabrication. The apparatus will determine the presence of defects in the pipe so that quality can be checked continuously as pipe is produced. Accordingly production of imperfect pipe is minimized.

Essentially, there are two embodiments of the invention. In an embodiment which is preferred when flaw inspection is immediately after pipe fabrication, the detector assembly is endless and surrounds the workpiece. For inspection of selected portions such as a pipe weld and where manufacture permits space between the pipe forming machine and a detector, a segmented detector arrangement is preferred.

The endless inspection apparatus is used with pipes and bars of a wide range of sizes. Pipe sizing operations used to form relatively small-sized workpieces cause the probability of a cobble to be relatively high. Accordingly, a rugged endless inspection apparatus is fixed to a sizing machine to serve as a guide to direct pipe out of the machine. In this manner the danger of a calamity resulting from a cobble is minimized.

Where the manufacturing operation permits the detector to be spaced from a pipe welder or sizer, the detection coils are positioned in movable groups in the manner described more completely in the DETECTOR CASE. This group arrangement not only minimizes the danger of cobbles, but also facilitates repair or replacement of elements of the detection system. There are further advantages to the multiple group arrangement which will be described presently.

One of the outstanding advantages of the present invention is the discovery that a nonmagnetic, metal heat shield may be interposed between a workpiece and a detection coil without any appreciable loss in flaw detection sensitivity. This discovery permits the construction of a detection assembly in which excellent heat transfer characteristics are achieved. This discovery is used to great advantage in both the embodiments.

A cooling medium is applied over the surface of the heat shield to maintain detection coils at a cool temperature. The combination of the cooling medium and the heat sensitivity characteristics of stainless steel makes the hot inspection of steel products of any size both reliable and practical for the first time. This combination also completely obviates the previously assumed need for special heat resistant materials or specially designed detection components.

In the endless detector assembly embodiment, a tubular, non-magnetic, stainless stell heat shield surrounds a workpiece path of travel. An annular support carries this heat shield. Exciter and detection coils are positioned within the support in spaced relationship with the heat shield to provide a detector assembly.

The support and shield are constructed to define an annular coolant flow path between the detection coils and the heat shield. Coolant flow is longitudinal and in a direction opposite to the path of travel of a pipe being inspected.

The annular coolant flow passage is constructed such that its radial dimension is greater at the inlet end than at the outlet to assure maintenance of appropriate velocity and pressure heads and to minimize vaporization of the coolant medium which could otherwise occur.

With the endless detector assembly small pipe embodiment of the present invention, the coolant outlet passages are directed radially inwardly. These outlet passages function as nozzles which direct streams of coolant medium onto the surface of a pipe immediately prior to flaw inspection. Coolant from these streams functions to clean the surface of the pipe and the detector, removing scale and other foreign matter which might deleteriously affect the flaw inspection operation. In addition, this coolant is carried with the pipe through the detector to flush scale and other foreign matter out of the detector assembly.

With the multiple detector group embodiment, a non-magnetic heat shield and fluid cooling are also used in either of two forms. In one form, a relatively small heat shield is provided which is, where detector sensitivity is optimized, contoured to the shape of the workpiece. This small shield is interposed between the detection coils and the workpiece path. Encapsulating fluid-impervious material surrounds the detection coils and is between the coils and the shield. Coolant is sprayed on this heat shield by nozzles positioned to direct the coolant circumferentially of the pipe.

In an alternate form of the multiple detector group embodiment, a tubular heat shield surrounds the workpiece path of travel. The detector groups are suitably biased against the heat shield. Each group has a series of nozzles that direct coolant circumferentially between the detection coils and the heat shield while the detection coils are maintained suitably spaced from the heat shield. Thus, in both embodiments of the invention, good results are achieved by taking advantage of the discovery that tubular non-magnetic heat shields may surround the workpiece path of travel.

As indicated previously, a cobble can result in catastrophe. With the present invention, a possibility of a cobble tearing out a detection system or even a component of it is practically completely eliminated.

One of the outstanding discoveries of the present invention is that excellent results are achieved with exciter coil segments being associated and movable with detector coils. These segments excite essentially only that portion of a workpiece being inspected by the associated detector coils.

Thus, each detector coil group carries its own exciter coil. Where only the weld is being inspected, only the weld area is excited. Where circumferential inspection is being carried on there will be as many exciter coils, or coil assemblies, as there are groups of detector coils. Accordingly, the detector and exciter coil assemblies can be shifted radially as far as needed to avoid a cobble when the workpiece departs from its intended path of travel. In addition, these assemblies may be removed individually for repair or replacement with relative ease and without interrupting a continuous manufacturing operation.

In its simplest form, the exciter coil is wound around a group of detector coils and the coils are then encapsulated in the fluid-impervious material. In a somewhat more sophisticated and preferred form, a group of exciter coil supports are provided. An exciter coil element is wound around each support. Each support is fixed to an associated detector element. The result is a relatively uniform spacing relationship of exciter and detector coils to workpiece. Adjacent exciter coils will have slightly overlapping exciter fields so that quite uniform workpiece excitation is achieved, although planar exciter coil segments are used.

The exciter coil and an associated detector coil are positioned such that the planar surfaces of the supports oriented towards the workpiece are each positioned tangentially of an imaginary cylinder. Each imaginary cylinder is concentric to the axis of the workpiece path of travel. The individual exciter and detector coils are wound on flat supports to facilitate manufacture and reproducible results. Nonetheless, the effect is quite similar to that achieved with a perfectly concentric exciter coil.

The use of groups of detector coils has other advantages which are described in the DETECTOR CASE. These include adjusting sensitivity according to the area being inspected. For example, one may have far greater detection sensitivity in the weld area than in the area of a pipe wall being inspected. Another is, in marking of the location of the defect, where the total pipe is being inspected, one gets an indication not only of the longitudinal location of the defect, but also an indication of circumferential location of the defect.

Another of the features of this invention resides in a novel marking technique which has been developed for marking hot workpieces. A conventional flocking or sandblast gun is used. Flocking and sandblast guns are quite similar in physical construction. While similar, they are intended for far different purposes than the marking of detected flaws in pipes and bars.

The marking gun used with the practice of this invention carries a quantity of atomized aluminum powder. The powder has a melting point of approximately 1200° F. A vibrator is connected to the gun to vibrate it on a continuous or substantially continuous basis. This vibration agitates the aluminum powder to facilitate its dispensing. This vabration supplements the material agitation achieved with air flow in the conventional gun and is especially desirable since air flow is quite intermittent occurring only when the flaw is detected.

When a flaw is detected, a signal from the detector actuates the marking gun. A short blast of cmpressed air expels a small quantity of aluminum powder from the gun and onto the pipe. Since the pipe is above the melting point of the aluminum, the powder is fused onto the surface of the pipe providing a highly visible indication of the location of a flaw with a marking material that can withstand the elevated temperatures of the workpiece.

Accordingly, the general object of this invention is the provision of eddy current flaw detection apparatus particularly suitable for nondestructive inspection and testing for undesirable flaws in articles at elevated temperatures and the method for operating such apparatus.

Other objects and a fuller understanding of the invention may be had by referring to the following description and claims taken in conjunction with the accompanying drawings.

BRIEF DESCRIPTION OF THE DRAWINGS

FIG. 1 is an exploded view of one preferred embodiment of the pipe eddy current flaw detection apparatus of this invention;

FIG. 2 is an end view of the assembled apparatus of FIG. 1 on an enlarged scale with parts broken away and removed;

DESCRIPTION OF THE PREFERRED EMBODIMENTS

The description is separated into separate subjects for convenience. These are:
A. The endless assembly.
B. The segmental assembly.
C. The heat shield.
D. The hot workpiece marker.

A. The Endless Assembly

The preferred embodiment of a flaw detector assembly where the detector is as close to pipe formation as possible is shown generally at 10 in FIGS. 1–4. The detector assembly 10 is annular and is secured to a pipe sizing machine shown schematically at 11 in FIG. 3.

Welded pipe 12 is continuously manufactured by the sizing machine 11. The pipe 12 is fed from the machine 11, travelling from left to right in FIG. 3 as indicated by arrows. The pipe travels along a workpiece path which has an axis indicated schematically by the dotted line 13. The detector assembly 10 is concentrically disposed about the pipe and is coaxial with it. The feeding of pipe from the sizer causes relative movement of the pipe and the detector assembly.

Figures 1, 2, 10:
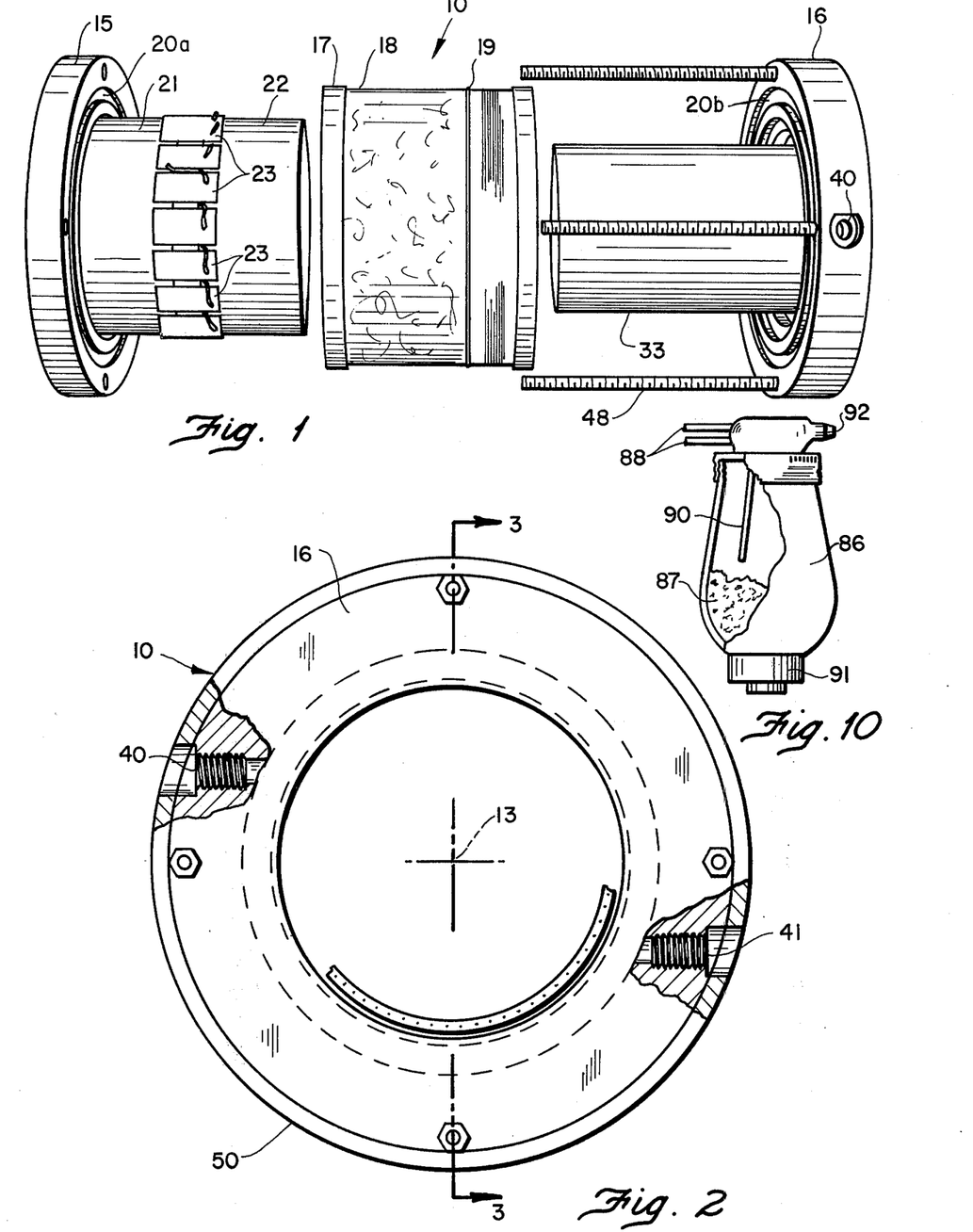

The detector assembly 10 has a pair of spaced end plates 15, 16. The end plates 15, 16 are annular and are formed to support the various components of the detector assembly.

An annular exciter coil support 17 is provided. The exciter coil support has a perimetral annular recess 18 formed in it. The annular recess extends, axially speaking, over a substantial portion of the exciter support 17. An exciter coil 19 is wound around the support 17 and postioned in the recess 18.

The end plates 15, 16 respectively have annular exciter coil mounting grooves 20a, 20b. These mounting grooves 20a, 20b locate and maintain the exciter coil support in a position which is coaxial with the workpiece path.

Figure 4:
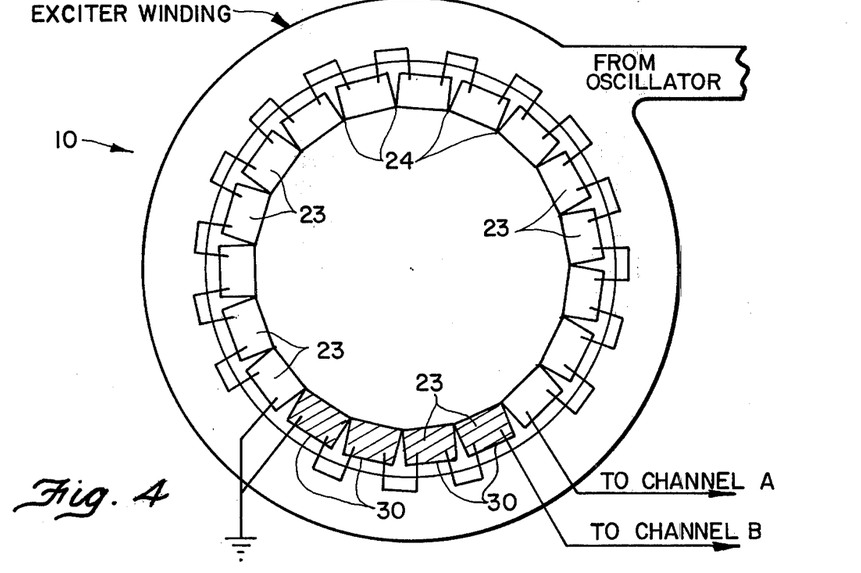
FIG. 4 is a diagrammatic illustration of the exciter and detector transducer assembly of the detection apparatus shown in FIGS. 1—3.

A pair of detector coil support rings 21, 22 are provided. A plurality of detector coil supports 23 are between and bonded to the support rings 21, 22. As is best seen in FIG. 4, the detector coil supports are each generally rectangular in cross section. They are positioned in an endless array with inside corners 24 in juxtaposition, FIG. 4. Thus the rings 21, 22 and the supports provide an annular endless and imperforate detector assembly.

Each detector coil support has three grooves 25 formed in it. A detector coil, not shown, is wound on each support in a known manner. The detector coil is wound in one direction in the outer grooves and in the opposite direction in the center groove. The total windings in the outer grooves equal the windings in the center groove so that the coil is balanced and output signals are emitted only when eddy current variations are sensed.

Figure 3:
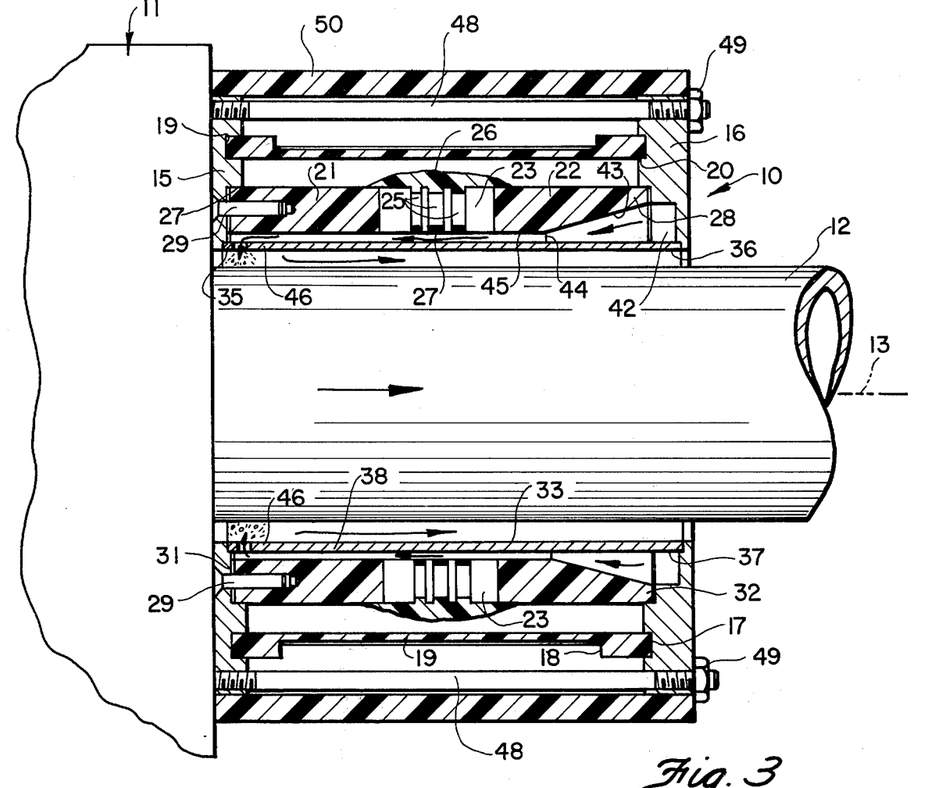
FIG. 3 is a sectional view of the apparatus shown in FIGS. 1 and 2 as seen from the plane indicated by the line 3—3 of FIG. 2.

Potting compound is applied around the detector coil supports as shown at 26 in FIG. 3. Similarly, potting compound is placed in the inner portions of the grooves 25 as shown at 27 in FIG. 3. In the finished detector coil assembly, the detector coils are hermetically sealed by the potting compound 26, 27.

A pair of detector assembly locating shoulders 27, 28 are formed in the end plates 15, 16, respectively. The detector assembly is circumferentially located by these shoulders so that it too is concentric about the workpiece path and coaxial with the workpiece axis 13. The detector assembly is secured to the end plate 15 by suitable fasteners 29 which thread into bores in the detector support 21.

A gasket 31 is interposed between the end plate 15 and the detector ring 21 to provide a fluid-tight seal. Similarly, a gasket 32 is interposed between the detector ring 22 and the end plate 16 to form a fluid-tight seal between them.

Referring now to FIG. 4, the detector supports 23 have inner planar surfaces. These surfaces are arranged such that their respective longitudinal centerlines, that is an imaginary line centrally spaced between each detector coil support's corner edges 24, are each tangential to an imaginary cylinder. This imaginary cylinder is concentric about the workpiece path of travel.

With this arrangement, any defect which is radially inward from a coil support centerline is at a location of minimum spacing between the workpiece and the detector coil. Accordingly, the sensitivity of the coils is maximized.

If, on the other hand, a defect is radially inwardly from a juncture of two corner edges 24, the spacing with the detector coils is maximized. Even though the spacing is maximized, the defect is in a location where it will cause signals in two detector coils and the sum of the two signals will be substantially equal to a maximum signal from the single coil. This arrangement is similar to that which is described and claimed in greater detail in the DETECTOR CASE.

The detector coil arrangement of FIG. 4 is designed for use with a welder which forms a weld at the bottom of the pipe. Four detector coil supports 23 are at the bottom of the detector assembly and designated by the numeral 30. The coils carried by the supports 30 are connected in series and to one channel, designated channel B, of a processing circuit. The remaining detectors are connected in series and connected to another channel, designated channel A, of a detector circuit. A suitable circuit is that described in greater detail in the CIRCUIT CASE.

The purpose of four coils 30 for weld inspection is to provide a circumferential range of weld inspection capability. The reason for this is that the weld tends to turn a bit. With this construction, the weld will always be between the longitudinal centerlines of the outer two of the detector coil assemblies 30.

An annular heat shield 33 is carried by the end plates. The end plates 15, 16 respectively have heat shield locating shoulders 35, 36 which locate the heat shield 33. The shield is in concentric relationship and coaxial with the workpiece path. The shield is preferably welded to the end plate 16 by a weld indicated at 37.

The heat shield is a circumferentially endless tube of non-magnetic metal material. The preferred material is 300 series stainless steel. The properties of the heat shield will be discussed in greater detail presently.

The heat shield is spaced from the detector assembly so that the two together define an anular coolant passage 38 between them. Coolant flows from right to left as viewed in FIG. 3. The coolant is supplied through coolant ports 40, 41, FIGS. 1 and 2.

The end plate 16 has an enlarged coolant inlet recess ring 42 with which the ports communicate. The exciter support ring 22 has tapered inner surface portion 43 which is frusto-conical. The tapered portion 43 has its larger end to the right as viewed in FIG. 3. The larger end is of a diameter substantially equal to the diameter of the coolant recess 42. The tapering surface 43 is of a diameter at its left-hand end 44 equal to the inside diameter of a cylindrical portion 45 of the support ring 22 and of the support ring 21. Thus, the end 44 is a junction of the portions 43, 45.

The tapering surface provides a coolant flow path of diminishing radial dimension in the direction of fluid flow, from right to left in FIG. 3. This diminishing radial dimension assures the maintenance of a good coolant velocity head and minimizes cavitation, vaporization of the coolant and other problems as the coolant passes through the remainder of the coolant passage. The remainder of the passage is a portion of substantially constant radial dimension. The portion of the coolant passage having substantially uniform radial dimension extends from the juncture 44 to outlet passages 46 formed near the left-hand end, as viewed in FIG. 3, of the heat shield 33.

A plurality of these outlet passages 46 are formed at circumferentially spaced locations in the heat shield. The passages 46 are near the left-hand end, as viewed in FIG. 3, of the detector 10. These passages 46 serve as nozzles to emit the coolant as substantially radially inwardly directed streams or jets that impinge on the tube 12. These jets tend to clean any loose scale or dirt off the surface of the workpiece. Perhaps more importantly, when the coolant is impinged on the steel pipe which is moving at relatively high speed from left to right, the coolant is carried with the pipe. As the coolant moves with the pipe along the workpiece path it purges foreign matter from within the detector and inhibits the build-up of scale deposits or other foreign matter within the heat shield 33.

The detector assembly is held together by suitable studs 48. The studs are threaded into the end cap 15. Nuts 49 are on stud ends which project past the end plate 16 to clamp the entire assembly together.

A protective cover sleeve 50 is slid over the entire assembly and suitably fastened in place. Fluid supply fittings connecting to the fluid inlets 40, 41 serve to locate the covering sleeve 50. In addition, removable fasteners not shown are used.

With the described assembly 10, repair can easily be achieved by disconnecting the outer sleeve 50 and removing the nuts 49. If the detector assembly requires servicing for example, one can simply remove the fasteners 29, lift out the detector coil assembly and insert another. Similarly, the exciter coil assembly can be lifted out and replaced.

B. The Segmental Assembly

FIGS. 5-9 show the detector assembly which is preferred when only the weld is to be inspected. The segmental assembly is preferred for circumferential inspection where the detector may be spaced from a welder and sizer.

Each of these figures shows a construction which takes advantage of one of the outstanding discoveries of this invention. That discovery is that an exciter and detector coil group can be manufactured as an assembly which is movable as a unit relative to a workpiece. Thus, for the first time the exciter coil is movable relative to a workpiece to facilitate repair and to avoid the calamity which can occur with a cobble.

Figures 5, 6, 7, 8, 9:
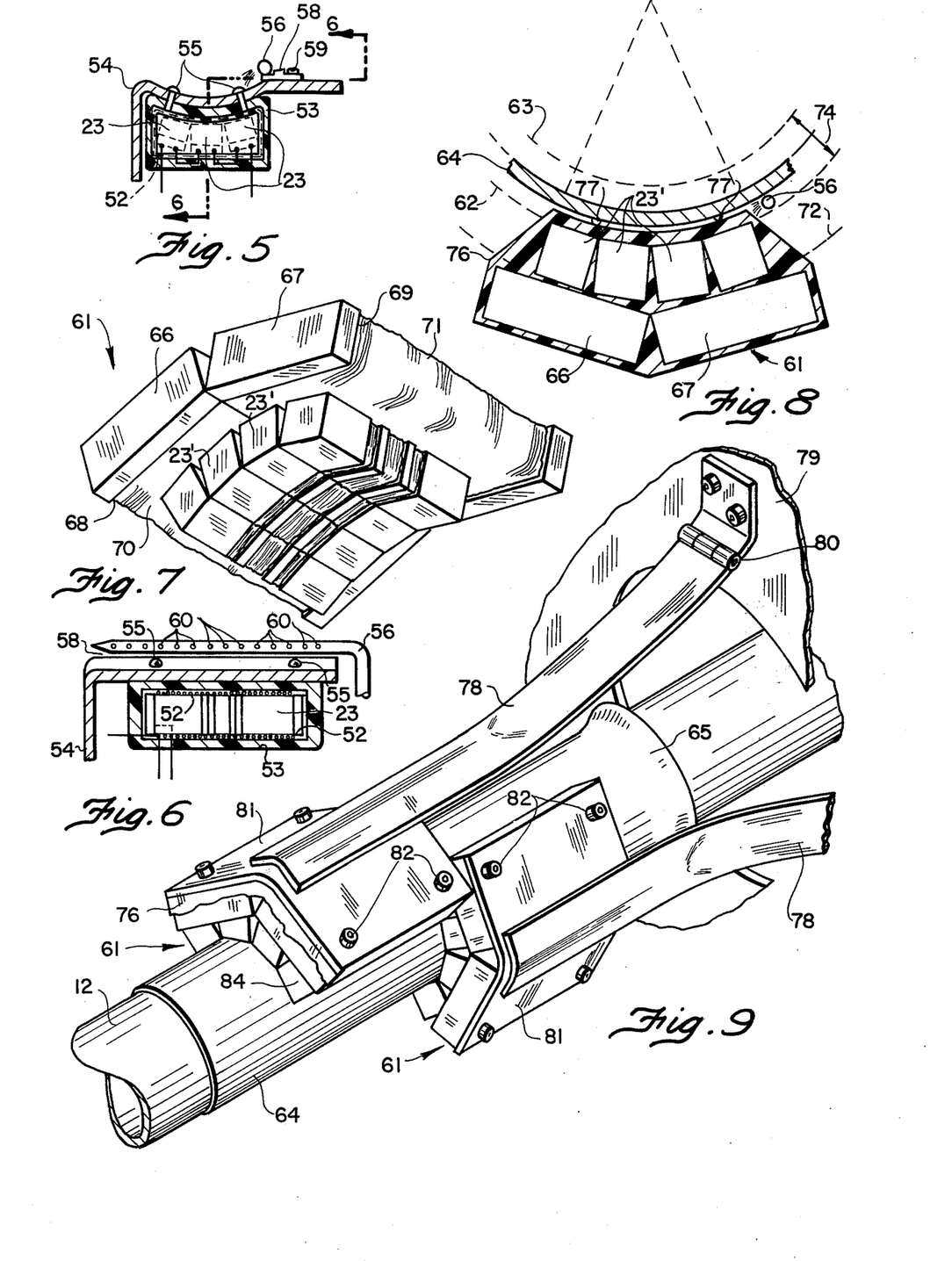
FIG. 5 is a sectional view of portions of another preferred embodiment of an eddy current flaw detection apparatus of this invention.
FIG. 6 is a sectional view of the apparatus shown in FIG. 5 as seen from the plane indicated by the line 6—6 of FIG. 5.
FIG. 7 is a perspective view of a coil assembly of a variation of the embodiment of FIGS. 5 and 6 of the eddy current flaw detection apparatus of this invention.
FIG. 8 is a sectional view of the apparatus shown in FIG. 7.
FIG. 9 is a perspective view of an ispection apparatus using the detector of FIGS. 7 and 8; and, FIG. 10 is a sectional view of the flaw marking spray gun.

In FIGS. 5 and 6, three detector coil supports 23 are shown. As the reference numeral indicates, these detector coil supports and the detector coils they carry are identical to those which have been described in connection with the embodiment of FIGS. 1-4. The coils carried by the three supports are series connected and in turn connected to a channel of a suitable processing circuit.

In this embodiment, an exciter coil, indicated schematically at 52, is wound directly around the detector coil supports. The detector coil supports 23 and the exciter coil 52 are encased in an hermetic envelope 53 for fluid protection. A heat shield 54 is suitably secured to the detector and coil assembly as by fasteners 55. The heat shield 54 is, like the heat shield 53, preferably made of non-magnetic material with the preferred material being 300 series stainless steel.

A coolant tube 56 is provided. The coolant tube 56 is carried by a coolant tube support 58. The coolant tube support 58 is secured to the heat shield 54 by suitable fasteners 59.

The coolant tube 56 has a plurality of outlet apertures 60. These outlet apertures 60 serve as nozzles directing coolant onto the heat shield 54. The nozzles emit the coolant which flows along a path that is circumferential with respect to a workpiece.

The coolant path is, like the path of coolant used in the embodiment of FIGS. 1-4, between the workpiece and the detectors to cool the heat shield. Cooling of the heat shield assures the maintenance of detector temperature levels which are low enough to to assure uniform and reliable flaw inspection.

Referring now to FIGS. 7-9, an exciter-detector coil assembly is shown generally at 61. The assemblies 61 each have four detector coil supports 23'. The supports 23' are generally square in cross section and are otherwise identical to the detector supports 23. The supports 23' are mounted such that their longitudinal centerlines are tangential to an imaginary cylinder indicated schematically by the dashed line 62 in FIG. 8. This dashed line is concentric with the perimeter of a workpiece indicated schematically by the dashed line 63.

A heat shield 64 is between the detector coils and the workpiece. For clarity of illustration, the heat shield is not shown in FIG. 7 and only a portion of it is shown in FIG. 8.

The heat shield 64 is an elongated tube through which a workpiece 12 passes. Mounting apparatus (not shown) secures the heat shield 64 in a concentric and coaxial relationship with the workpiece path, in a manner analogous to that of the heat shield 33 of FIG. 3. The tube has a flared portion 65 at its inlet end which serves to guide the workpiece into the tube. Thus, with the exciter-detector coil assembly 61, or the exciter-detector assembly shown in FIG. 5, one may have either a circumferential endless heat shield 64, or the small heat shield 54, mounted to move with the detector coil assembly.

A pair of exciter coil supports 66, 67 are provided. The exciter coil supports 66, 67 are of generally rectangular configuration. The exciter coil supports 66, 67 respectively have perimetral grooves 68, 69 formed in them which extend for a major portion of the length of the supports. A pair of exciter coils 70, 71 are respectively wound around the supports 66, 67 and positioned in the grooves 68, 69.

The exciter coil supports, in a manner similar to the detector coil supports, are positioned such that their respective longitudinal centerlines are tangential to an imaginary cylinder. This imaginary cylinder is indicated schematically by the dashed lines 72 in FIG. 8.

Expressed another way, the heat shield is contoured to a configuration of the workpiece so that it is substantially uniformly spaced from it. Similarly, the exciter and detector coil supports are respectively positioned such that their longitudinal centerlines are tangential to an imaginary configuration which is of a contour corresponding to that of the workpiece and these supports are uniformly spaced from the workpiece. This assures substantially uniform excitation of the workpiece and substantially uniform detection response.

Although the exciter coils need not be contoured to a configuration corresponding to that of the workpiece, as has generally been the case in the past, they function in a substantially equivalent manner. For example, a point on a workpiece surface equally spaced from exciter coil support centerlines is excited by both exciter coils. Thus, although such a point may be further from an exciter coil than a corresponding point radially inwardly from an exciter coil support centerlines, the excitation is substantially equal because of the overlapping of the excitation of the two coils.

The detector coil supports are spaced from the workpiece a distance indicated by arrow 74. This distance is minimized to improve detector efficiency. In practice, the distance must be nominally of the order of one quarter of an inch or larger to allow for variations due to such things as workpiece out-of-roundness and the fact that the workpieces are not always straight.

The exciter and detector coils of FIGS. 7 and 8 are encapsulated in a potting compound 76 shown only in FIG. 8 for clarity. Spacers 77 maintain a spacing between the potting compound 76 and the heat shield 64. Coolant is sprayed between the two by the coolant tube 56.

The exciter-detector assembly 61 is movably mounted with respect to the heat shield 64. They are each mounted on a different one of arms 78. The arms 78 are each pivotally connected to a support 79 by a suitable hinge or other pivot 80. Each arm 78 carries a detector support shoe 81. The exciter-detector assemblies 61 are connected to their respective support shoes 81 by fasteners 82.

In the version shown in FIG. 9, the exciter-detector assemblies 61 are biased against a tubular heat shield. Where the individual heat shields 54 are provided, the detector assemblies are biased against a stop or, if the workpiece is not a hot workpiece, the assemblies may be biased against the workpiece. When they are biased against a workpiece, a wear shoe may be used as taught in the referenced patent. When the supporting arms 78 are biased against stops, the stops may be constructed in the manner taught in the DETECTOR CASE.

The biasing of the exciter-detector assemblies into their detection positions is accomplished in either of two ways. Where the exciter-detector coil assembly is above the pipe, gravity effects the biasing as taught in the referenced patent and as shown in FIG. 9. Alternately, and especially where circumferential pipe inspection is being performed, biasing structures such as the air cylinders shown and described in the DETECTOR CASE are employed.

The exciter-detector assemblies are positioned in overlapping relationship in the manner taught and claimed in the DETECTOR CASE with respect to detector coils. Thus, the longitudinal centerline of a lower one 84 of the detector coil supports 23 in the left-hand exciter-detector coil assembly of FIG. 9 is aligned with the longitudinal centerline of the upper one of the four detector coil supports 23 of the other assembly 61 of FIG. 9. With this alignment the exciter-detector coil assemblies inspect overlapping workpiece areas. Any point on the workpiece will pass either immediately under a longitudinal centerline of a detector support or between two of such centerlines of one of the exciter-detector assemblies. This assures relatively uniform sensitivity in the detection of flaws throughout the circumferences of the pipe.

C. The Heat Shield

As has been indicated, the heat shields 33, 54 and 64 are all preferably formed of nonmagnetic 300 series stainless steel. What has been discovered is that one may encircle a workpiece with a metallic heat shield without having an adverse effect on detection sensitivity. In short, it has been discovered that a metal liner can be used which will not act as an electro-magnetic shield.

One possible partial explanation of the theory involved in selecting a heat shield has been developed. According to this theory, when a solid round test piece is placed in an alternating electro-magnetic field, eddy currents flow in the entire cross section of the round except for the center. The majority of the eddy currents flow in the outer portion of the round. The round could be replaced with an imaginary hollow sleeve in which enough of the eddy currents would flow to make the sleeve appear, to the inducing source, to be essentially the same as the round.

The radial dimension of such an imaginary sleeve can be calculated. Where the radial thickness of the sleeve is indicated by the depth $d$, the formula:

$$d = 3160 \sqrt{\frac{R}{Uf}}$$

R — is resistivity in ohm-inches
U — the relative magnetic permeability
f — the frequency in cycles per second
d — reference depth in inches It has been discovered that the thickness of the heat sleeve must be several times less than $d$ to achieve good detection efficiency and to avoid any noticeable effect on test results. Typical $d$ values for a test frequency of 4000 hz, the frequency used in tests which have been conducted, are listed below:

| | |
|---|---|
| Nonmagnetic Stainless steel | 0.250" |
| Magnetic stainless steel | 0.009" |
| Low carbon steel | 0.004" |
| Brass | 0.08" |
| Aluminum | 0.053" |
| Copper | 0.04" |

If this theory is a correct explanation of a phenomenon that has been discovered, the preceding table makes it apparent why nonmagnetic stainless steel is preferred.

D. The Hot Workpiece Marker

In the past, a variety of automatic markers have been used to mark the location of a detected flaw in a workpiece. Typically, after a flaw has been detected, the marker is actuated a predetermined time delay after the detection has occurred. The length of the time delay is a function of the speed of the workpiece and the spacing of the marker from the detector. The marking is applied to the workpiece as close as possible to the flaw which has been located to assist workers in locating a detected flaw. Once a flaw is located, the workpiece is repaired or that segment of the workpiece in which an unacceptable flaw is located is scrapped.

A variety of marking techniques have been employed. One has been a spray gun which sprays paint on the workpiece in the vicinity of the flaw. Another has been to use various cutting or grinding tools to physically remove some metal and form a mark in the surface of the workpiece. All known prior detecting device have unacceptable disadvantages when the workpiece to be marked is a hot steel pipe traveling at speeds of the order of 1600 feet per minute.

A novel and unique melthod and apparatus for marking the workpiece has been devised. The apparatus uses a flock gun shown schematically at 86 in FIG. 10. One suitable flock gun is sold commercially under the model number GB-503 by DeVilbiss.

In the present case, the flock gun carries a quantity of aluminum powder having a melting point of approximately 1200° F. When the powder is sprayed on a hot workpiece which is at temperatures above the melting point of the aluminum powder, the aluminum fuses and provides a very visible mark.

The detectors are, as we have indicated, coupled to circuits of the type shown in the CIRCUIT CASE. These circuits are used to control the flock gun 87 in timed relationship with detection of a flaw. Air is supplied through control tubes 88 in a manner conventional for spray guns.

Air is supplied thorugh a dip tube 90 in the spray gun to agitate the atomized aluminum. In addition, a vibrator 91 is connected to the spray gun 86 to agitate the aluminum further. The combined effects of the agitation by air and vibration assure a good dispersion of the atomized aluminum in the gun. With this good dispersion, injection of a pulse of air to emit powdered aluminum spray through nozzle 92 will produce good and uniform results.

SUMMARY

A novel flaw inspection apparatus utilizing eddy currents has been described. The apparatus is especially suited for inspecting hot workpieces and utilizes the discovery that a metal heat shield can be interposed between a workpiece and detector without deleterious effect on detection efficiency.

Although the invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. An eddy current detector for inspecting hot steel pipe or the like passing along a workpiece path of travel comprising:
   a. a pair of spaced annular end plates;
   b. a circumferentially endless, tubular, metallic, non-magnetic heat shield surrounding the workpiece path and carried by the end plates;
   c. a detector assembly carried by the end plates in circumferentially spaced relationship to at least a portion of the heat shield thereby defining a flow passage therebetween;
   d. an exciter connected to the detector assembly and positioned sufficiently close to the path to induce eddy currents in a workpiece; and,
   e. said detector including inlet and outlet passages for conducting fluid into and out of the flow passage, said outlet passages being directed toward the workpiece path.

2. The device of claim 1 wherein at least a portion of the flow passage had radial dimensions which are diminishing in the direction of fluid flow.

3. The apparatus of claim 1 wherein said detector assembly is annular.

4. The apparatus of claim 1 wherein the heat shield is stainless steel.

5. The apparatus of claim 4 wherein the stainless steel is 300 series.

6. The apparatus of claim 1 wherein said heat shield and said workpiece also define a flow passage, fluid thereby flowing between the detector assembly and the shield and between the shield and the workpiece.

7. Eddy current flaw testing apparatus for detecting flaws in an elongated hot article as it is moved along a test path comprising:
   a. a body having an inner wall defining a central aperture surrounding the test path;
   b. said body defining a chamber about the test path;
   c. an exciter mounted in said chamber;
   d. a detector assembly including a plurality of detectors supported within said chamber, the detector assembly being mounted about at least a portion of the test path to detect distortions in the pattern of eddy currents induced in a workpiece by said exciter;
   e. said detector assembly being spaced radially inward from said exciter;
   f. said detector assembly and said inner wall together defining a passage substantially the longitudinal length of said body;
   g. means for the circulation of a cooling medium through said passage to maintain said detectors at a temperature below the hot article; and,
   h. a plurality of apertures in said inner wall providing outlets for said circulated cooling medium and for directing the medium toward the path onto a workpiece whereby the coolant will be carried by the workpiece to wash away deposits on said inner wall.

* * * * *

UNITED STATES PATENT OFFICE
CERTIFICATE OF CORRECTION

Patent No. 4,024,470          Dated May 17, 1977

Inventor(s) Joseph P. Vild, William I. Cleary, Donald P. Fox

It is certified that error appears in the above-identified patent and that said Letters Patent are hereby corrected as shown below:

Column 11, line 1, "centerlines" should be -- centerline --

Column 12, line 64, "device" should be -- devices --

Column 13, line 5, after "aluminum powder" insert -- 87. The aluminum powder is type 101 atomized aluminum powder --

Signed and Sealed this

Twenty-ninth Day of November 1977

[SEAL]

Attest:

RUTH C. MASON          LUTRELLE F. PARKER
*Attesting Officer*          *Acting Commissioner of Patents and Trademarks*